US012667457B2

(12) United States Patent
Perez et al.

(10) Patent No.: US 12,667,457 B2
(45) Date of Patent: Jun. 30, 2026

(54) INTRAOCULAR LENS DELIVERY SYSTEM PACKAGING

(71) Applicant: Johnson & Johnson Surgical Vision, Inc., Irvine, CA (US)

(72) Inventors: Yasemar Perez, Aguadilla, PR (US); Rodney Patch, Jacksonville, FL (US)

(73) Assignee: JOHNSON & JOHNSON SURGICAL VISION, INC., Irvine, CA (US)

( * ) Notice: Subject to any disclaimer, the term of this patent is extended or adjusted under 35 U.S.C. 154(b) by 502 days.

(21) Appl. No.: 18/335,887

(22) Filed: Jun. 15, 2023

(65) Prior Publication Data

US 2023/0404745 A1     Dec. 21, 2023

Related U.S. Application Data

(60) Provisional application No. 63/366,457, filed on Jun. 15, 2022.

(51) Int. Cl.
*A61F 2/16* (2006.01)

(52) U.S. Cl.
CPC ............ *A61F 2/1691* (2013.01); *A61F 2/167* (2013.01)

(58) Field of Classification Search
CPC ...... A61F 2/1691; A61F 2/167; A61F 2/1662; A61F 2250/0069; A61F 2250/0085
See application file for complete search history.

(56) References Cited

U.S. PATENT DOCUMENTS

| | | | | |
|---|---|---|---|---|
| 4,257,521 A | * | 3/1981 | Poler | A61F 2/1691 206/5.1 |
| 5,092,478 A | * | 3/1992 | La Pierre | B65D 41/48 220/276 |
| 7,954,636 B2 | | 6/2011 | Vincent-Aubry | |
| 2007/0250068 A1 | * | 10/2007 | Vincent-Aubry | A61F 2/1678 606/107 |
| 2009/0032489 A1 | * | 2/2009 | Moy | B65B 3/003 215/355 |

FOREIGN PATENT DOCUMENTS

| | | |
|---|---|---|
| EP | 2599460 A2 | 6/2013 |
| WO | 0221965 A1 | 3/2002 |

* cited by examiner

*Primary Examiner* — Richard G Louis
(74) *Attorney, Agent, or Firm* — TROUTMAN PEPPER LOCKE LLP

(57) ABSTRACT

Sterile packaging for an intraocular lens (IOL) delivery system includes a sealed container with an IOL delivery system contained therein, with a cap sealing the container. One or more tamper-evident solutions are provided on the packaging to ensure an indication of non-sterility. This configuration solves certain issues with prior packaging, such as clumsy transfers and bulky packaging which creates storage issues and mitigates sterility barrier risk associated with pouch or blister packaging or other non-rigid package types.

24 Claims, 15 Drawing Sheets

INTRAOCULAR LENS DELIVERY SYSTEM PACKAGING

CROSS-REFERENCE TO RELATED APPLICATIONS

This application claims the benefit under 35 U.S.C. § 119(e) of U.S. Provisional Patent Application No. 63/366,457, filed Jun. 15, 2022, which is incorporated herein by reference in its entirety.

FIELD OF THE INVENTION

The present invention relates to IOL delivery systems and, more particularly, to sterile packaging therefor.

BACKGROUND OF THE INVENTION

Intraocular lenses (IOLs) are commonly implanted in the eye as a replacement for the natural crystalline lens after cataract surgery. The IOL provides the light focusing function originally undertaken by the crystalline lens. Insertion of an IOL for the treatment of cataracts is the most commonly performed ophthalmic surgical procedure.

A typical IOL includes a disc-shaped optic or lens body for focusing light toward the retina of the eye. In addition, the IOL also includes one or more fixation members or haptics extending outward from the optic for securing and centering the IOL in the desired position within the chamber of the eye. The IOL is implanted directly into the eye through a small incision in a way that reduces trauma and expedites post-surgery healing.

To fit through this small incision, modern IOLs are designed to be deformed, e.g., rolled, folded or the like, to a relatively small profile prior to insertion into the eye and then allowed to return to their original shape within the eye. This process is efficiently done with a syringe-like injector having a narrowing injection tube through which the IOL is folded and then ejected using a push rod. The injector may have a handpiece that receives a cartridge, or the two may be integrated. Some separate cartridges are pre-loaded with an IOL.

The handpiece and cartridge, separately or pre-assembled, remain in a sterile package until ready for use. The current packaging system involves storing the sterile injector components in blister packs—flexible pouches that can be torn open. Anyone can handle the intact blister pack, but once opened the injector components should only be handled in a sterile environment by someone who has sterile garb and gloves. Thus, the process often involves a technician opening the blister pack over and dropping the injector components onto a sterile tray, after which they can only be handled by the clean technicians. This is cumbersome and introduces risks such as breakage and dropping. Moreover, ophthalmologist offices, clinics and hospitals that perform IOL replacements typically maintain a comprehensive supply of IOLs. The current packaging with blister packs for preassembled handpiece and cartridges are relatively bulky, create a legitimate storage space problem.

In view of the above, there is a need for a better way to store IOL injectors in a sterile package and transferring the injector to the sterile environment with less risk.

SUMMARY OF THE INVENTION

The present application provides compact, sterile packaging for an intraocular lens (IOL) delivery system. The sterile packaging includes a compact sealed container with a transfer tray therein. An IOL delivery system is held on the transfer tray within the container, with a cap sealing the container. One or more tamper-evident solutions are provided on the packaging to ensure an indication of sterility or non-sterility. The transfer tray is contoured to hold the IOL delivery system in a secure orientation, and is also coupled to the cap of the container. After opening the cap, the subassembly of the IOL delivery system and transfer tray may be removed from the container in a secure and safe manner. A user may then present the subassembly to a technician in a sterile environment, and the subassembly is easily decoupled from the container. This solves certain issues with prior packaging, such as clumsy transfers and bulky packaging which creates storage issues.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

Figure 1:
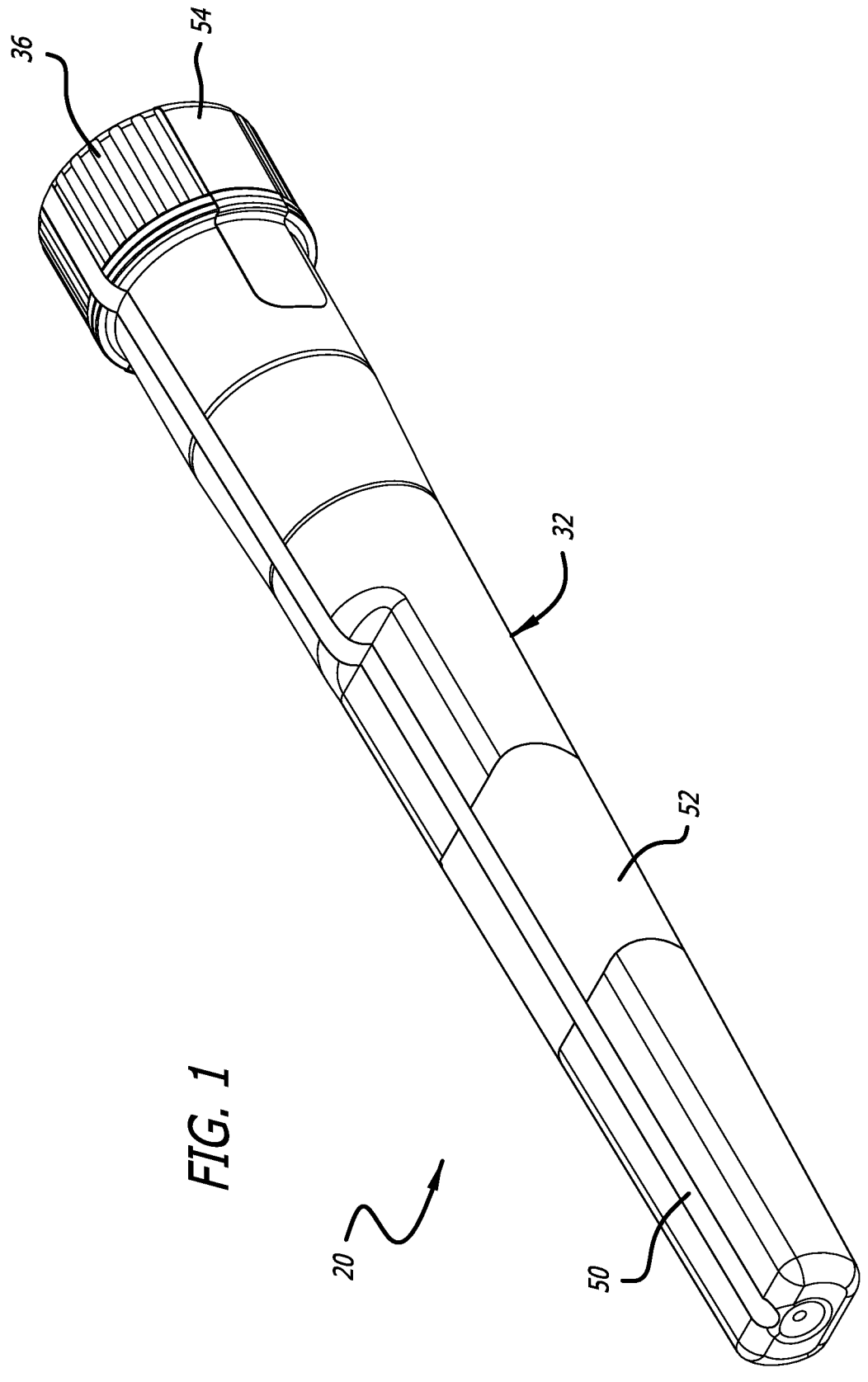
FIG. 1 is a perspective view from a distal end of a compact intraocular lens (IOL) delivery system sterile package in a closed configuration.
Figure 2:
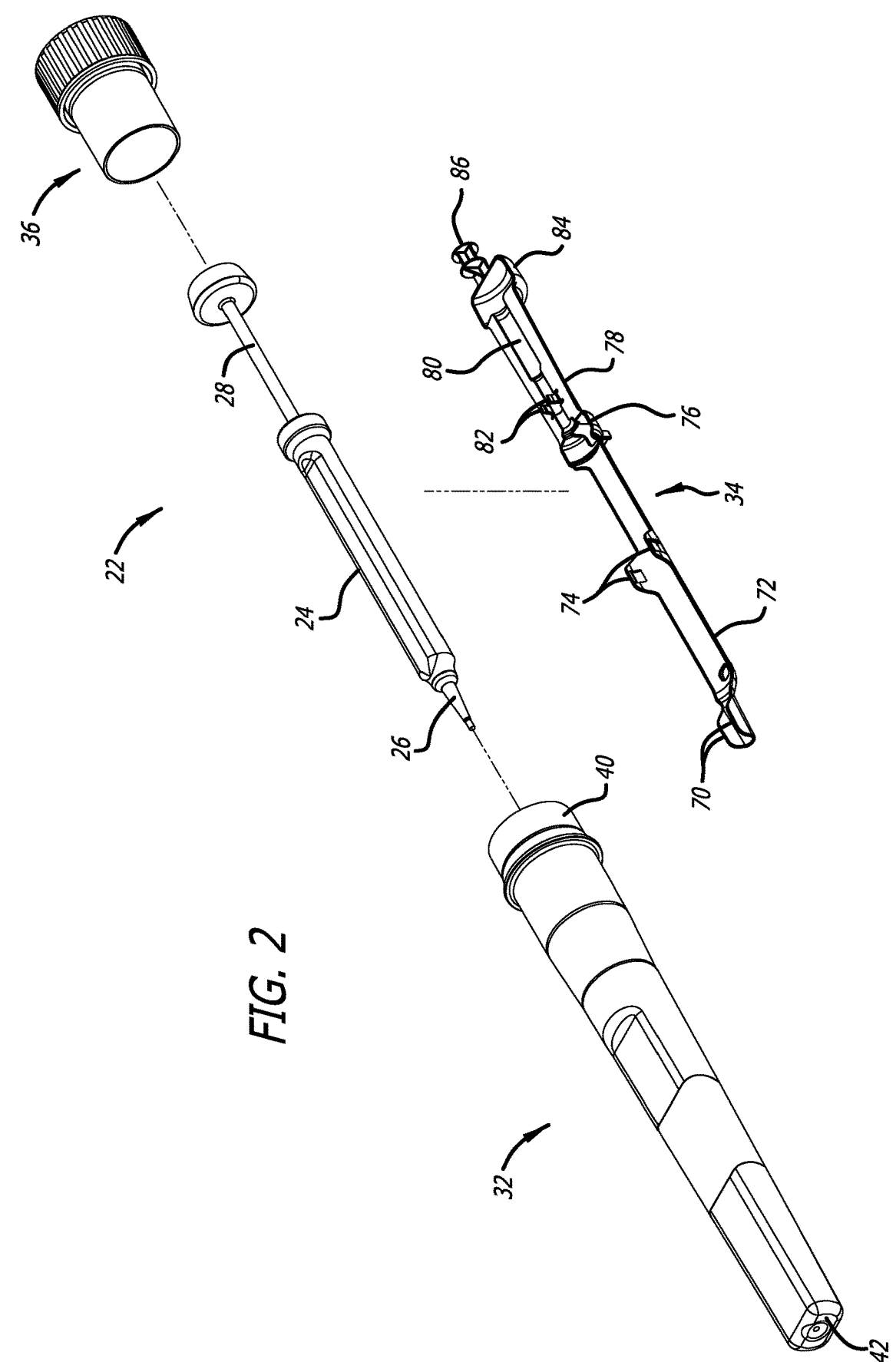
FIG. 2 is a perspective view of a compact IOL delivery system exploded from the components of the sterile package of FIG. 1.
Figure 12:
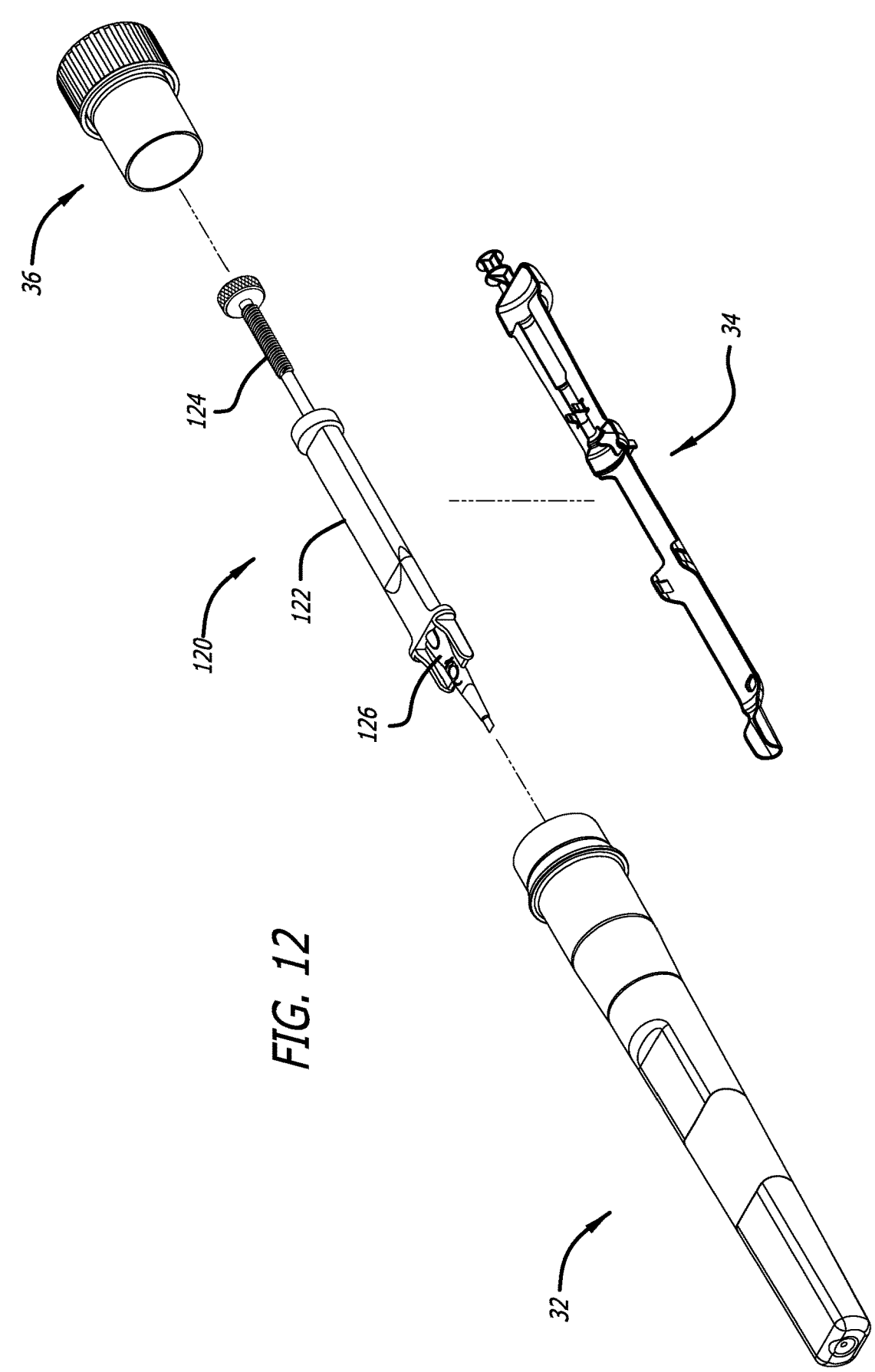
FIG. 12 is a perspective view of a first alternative compact IOL delivery system exploded from the sterile package components.
Figure 13:
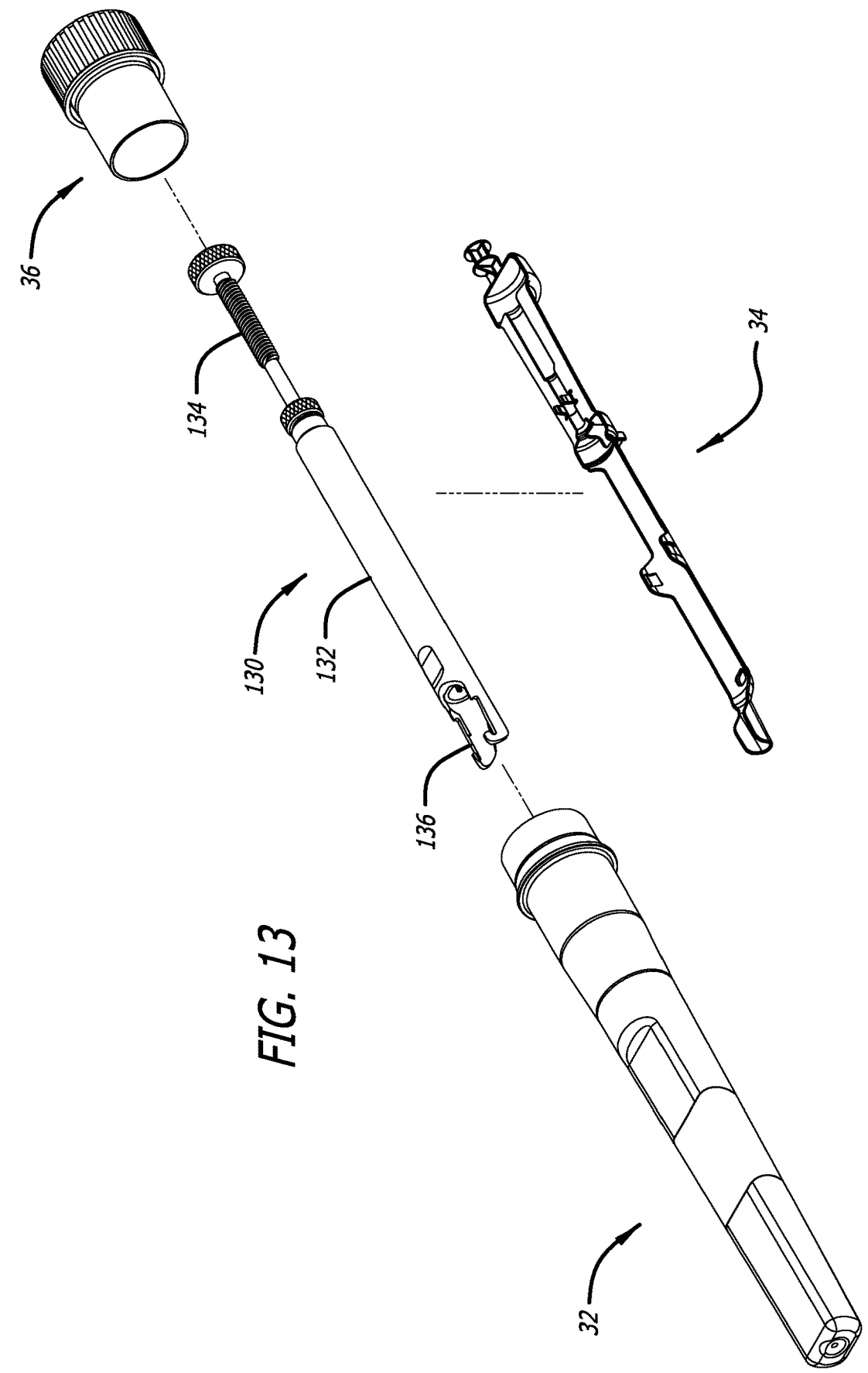
FIG. 13 is a perspective view of a second alternative compact IOL delivery system exploded from the sterile package components.

FIG. 1 is a perspective view from a distal end of an intraocular lens (IOL) delivery system sterile package 20 in a closed configuration, while FIG. 2 shows the IOL delivery system 22 exploded from the components of the sterile package. In a first embodiment, the IOL delivery system 22 comprises a syringe-like integrated assembly of an injector and an IOL (not shown). More particularly, the delivery system 22 includes a syringe body 24 having a tapered distal tip 26. An IOL may be placed within the syringe body 24 at the time of surgery, or may be pre-assembled therein. A plunger rod 28 is then used to urge the IOL from within the syringe body 24 through the distal tip 26 into the patient's eye. There are a number of such IOL delivery systems 22, and the present disclosure of sterile package intends to encompass all varieties. For example, FIGS. 12 and 13 illustrate two common alternatives. An intraocular lens (IOL) delivery system can be defined as either an integrated injector with the cartridge built-in, an IOL injector with and without an IOL cartridge, and an IOL cartridge with a distal inserter tip, such as the SmartLOAD™ delivery device available from Johnson & Johnson Surgical Vision, Inc. of Irvine, CA.

Figure 6:
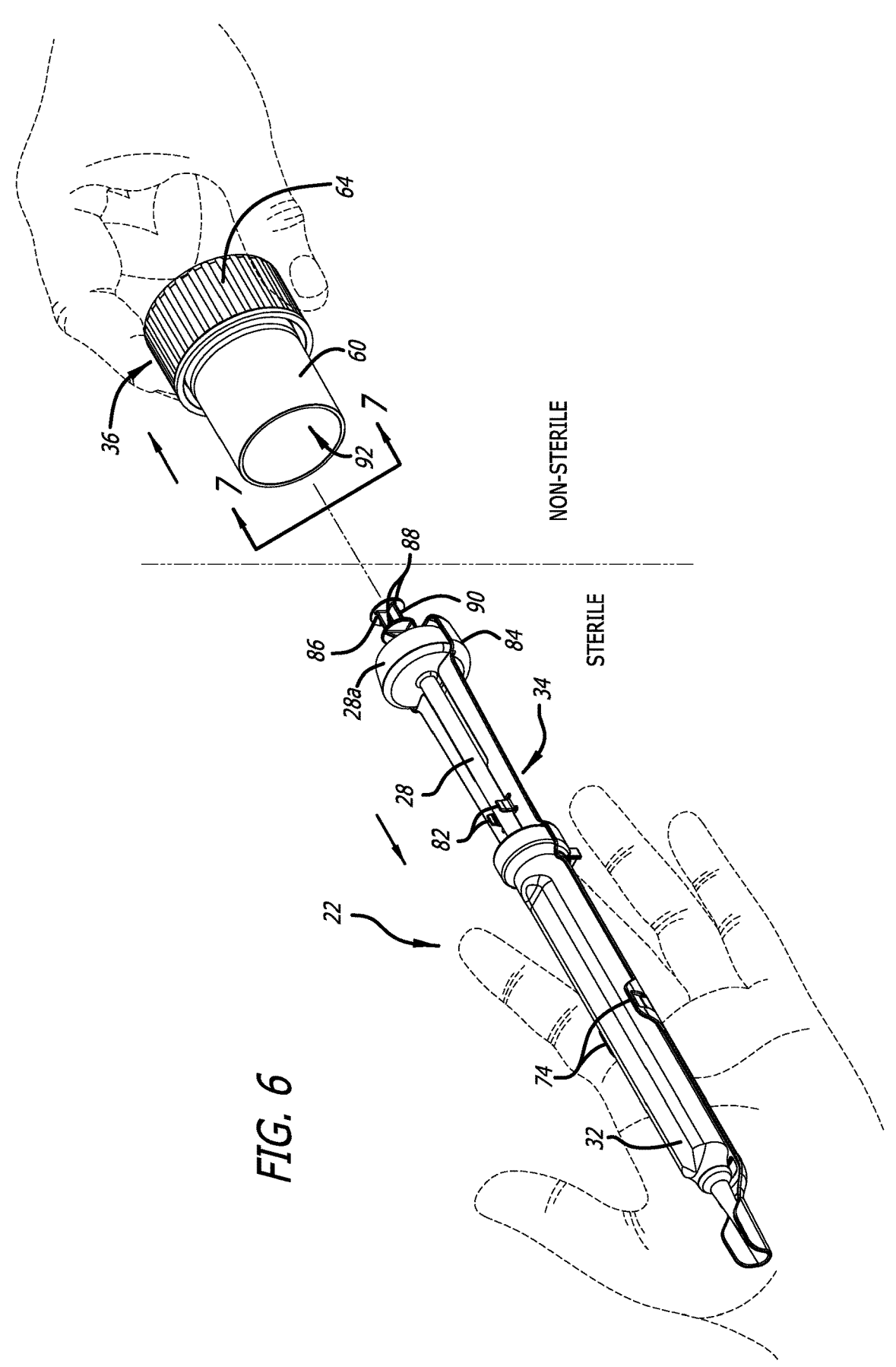
FIG. 6 is a perspective view of the compact IOL delivery system held within a transfer tray and shown being separated from a cap of the sterile package at the moment of transfer between a non-sterile environment to a sterile environment.

The sterile package 20 primarily comprises an elongated, generally tubular container 32, a transfer tray 34, and a proximal end cap 36. The transfer tray 34 is shaped to receive and retain the IOL delivery system 22 in a subassembly, as seen in FIG. 6, and the generally tubular container 32 has an inner cavity with the diameter and length sufficient to receive the subassembly. The generally tubular container 32 is gradually tapered from a wide, circular open mouth 40 at a proximal end to a narrow, closed distal end 42. The open mouth 40 is formed by a proximal end of a lumen defined by a wall of the tubular container 32 that extends in a distal direction in a first length. Though a tapered profile for the container 32 serves to constrain the subassembly from movement, other solutions such as inner bulkheads or the like may be used with a cylindrical or otherwise non-tapered profile. The inner cavity of the container 32 may be shaped to closely receive the subassembly of the IOL delivery system 22 and transfer tray 34 such that little or no relative movement is permitted when the subassembly is received in the container. Prior to a more detailed discussion of the components of the sterile package 20, a sequence of disassembly will be explained.

Figure 3:
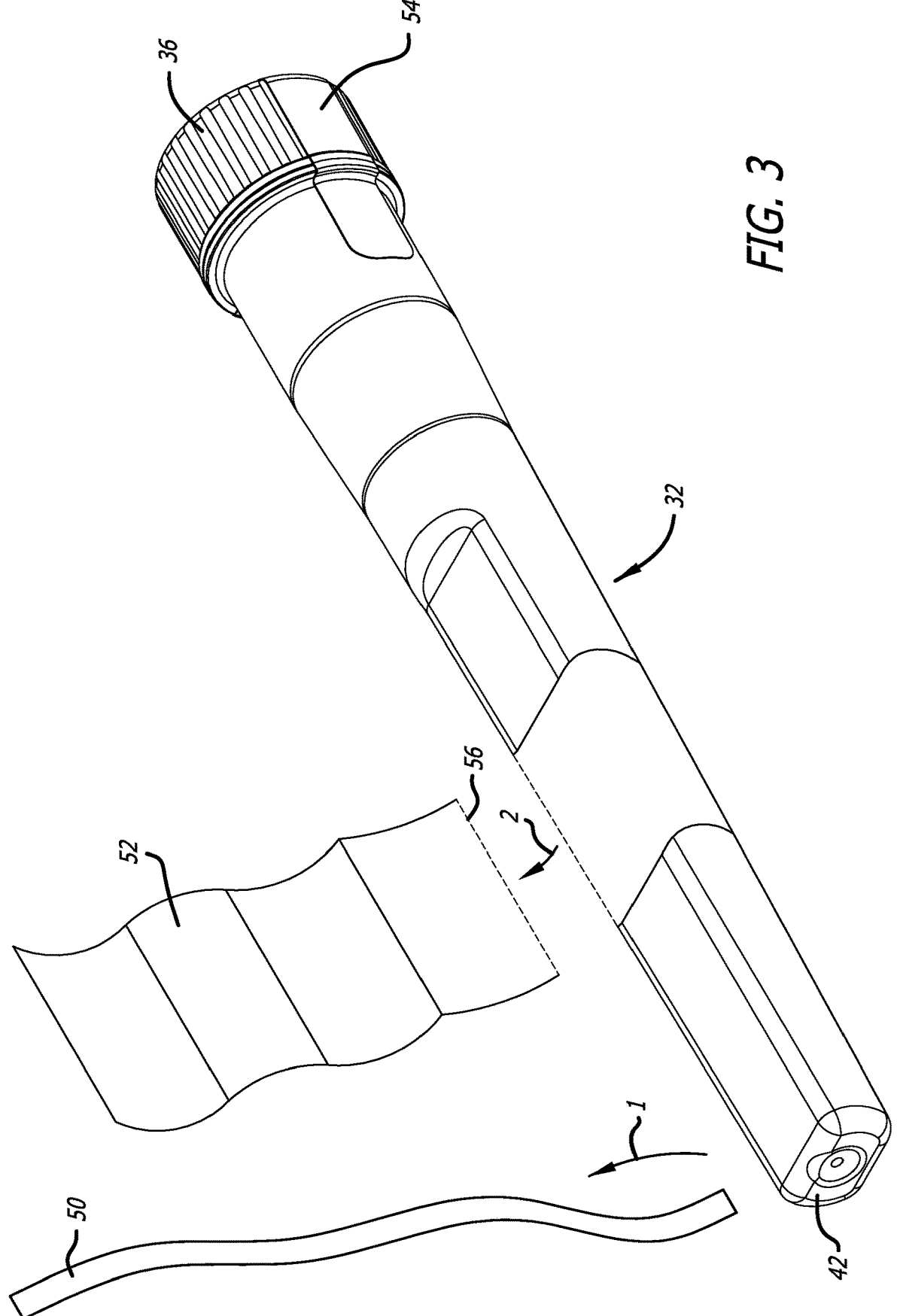
FIG. 3 shows the compact IOL delivery system sterile package after removal of a first tamper-evident strip, and removal of an identification label.

FIG. 3 shows the sterile package 20 after removal of a first tamper-evident strip 50, and removal of an identification label 52. As seen in FIG. 1, the first tamper-evident strip 50 extends longitudinally from the closed distal end 42 on the outside of the container 32, over the identification label 52, and wraps around in terminates on a proximal end of the proximal end cap 36. FIG. 1 also shows a shorter second tamper-evident strip 54 that extends longitudinally along a proximal portion of the container 32 and also wraps around the proximal end of the proximal end cap 36. The two tamper-evident strips 50, 54 provide a redundant system which maintain an indication of sterility of the package 20 until usage and alerts a technician if the package has been tampered with. More than the two tamper-evident strips 50, 54 may be provided around the proximal end cap 36 for added security. For instance, a tamper-evident solution such as a shrink wrap film may also cover most of the body. Removal of the first tamper-evident strip 50 may also remove the shrink wrap film.

The first tamper-evident strip 50 is desirably secured to the package 20 as part of a full body shrink-wrapped cover (not shown), not as a stand-alone feature. The typically clear shrink wrap cover goes over the all or part of the body of the package, and the strip 50 is a pre-perforated section of the shrink wrap material which is easily separated from the rest of the cover, thus allowing removal of the cover. That is, the strip 50 and shrink wrap cover can be removed in one piece. The second tab-evident strip 54 may be adhered along the entire length and width, as it is not torn away from the package 20 but instead ruptured at a midpoint, as will be described below.

After removal of the first tamper-evident strip 50, as in FIG. 3, the user may pull the identification label 52 away from the container 32. The label 52 provides identifying information such as IOL delivery system model, IOL model diopter, expiration date, serial number, batch number, manufacture date, a bar or QR code, etc. Additionally, the label 52 desirably comprises several alternately folded panels on which is provided same information in several different languages. Also, the label 52 may include smaller peel away labels containing IOL information to be used in the patients record. It also may include a patient implant card or other printed material information as required by regulations. Finally, the label 52 may be completely separated from the container 32 at a tear or perforation line 56.

Figure 4:
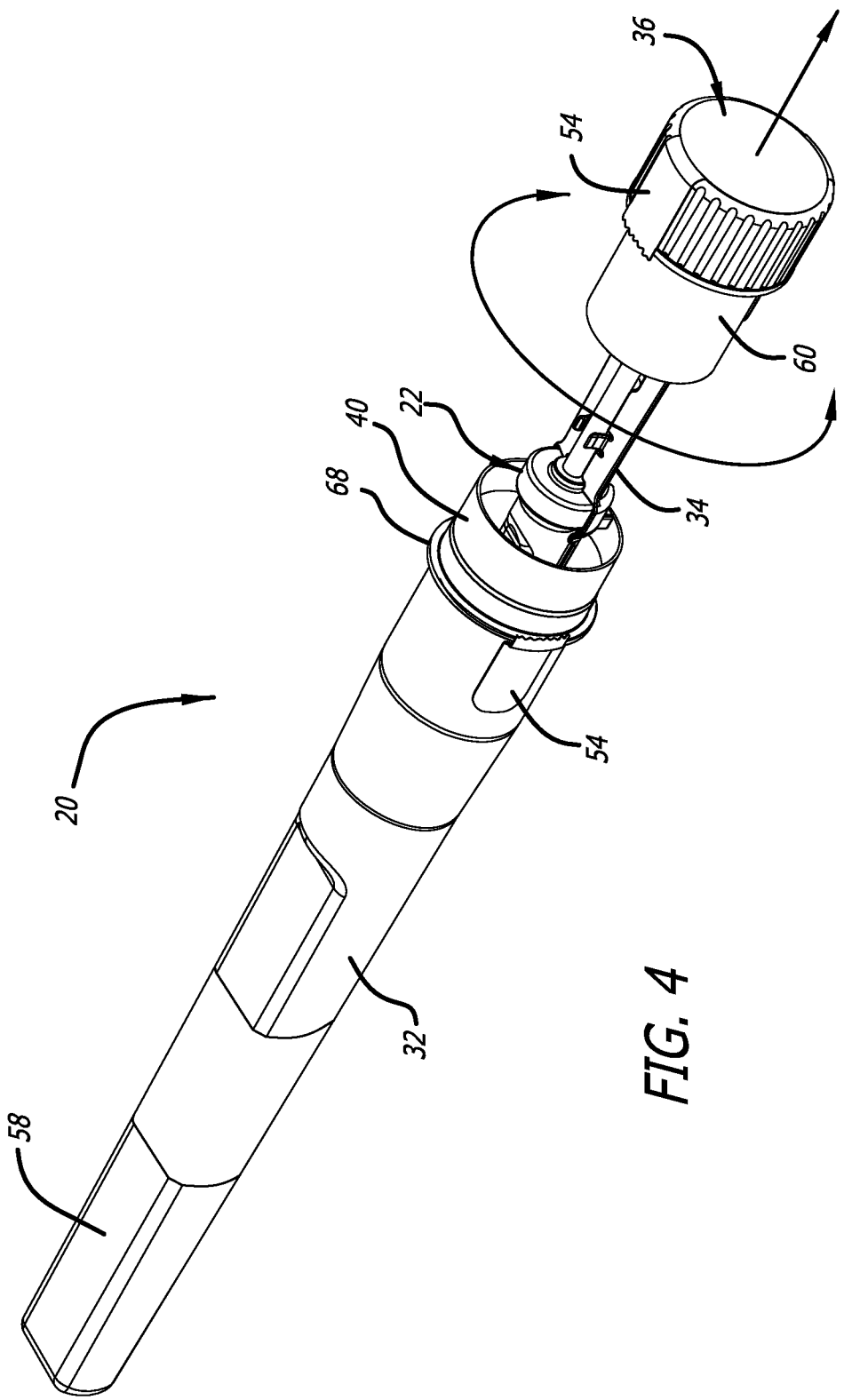
FIG. 4 is a perspective view from a proximal end of the compact IOL delivery system sterile package after a step of breaking a second tamper-evident strip and partial removal of the IOL delivery system from the sterile package.
Figure 5:
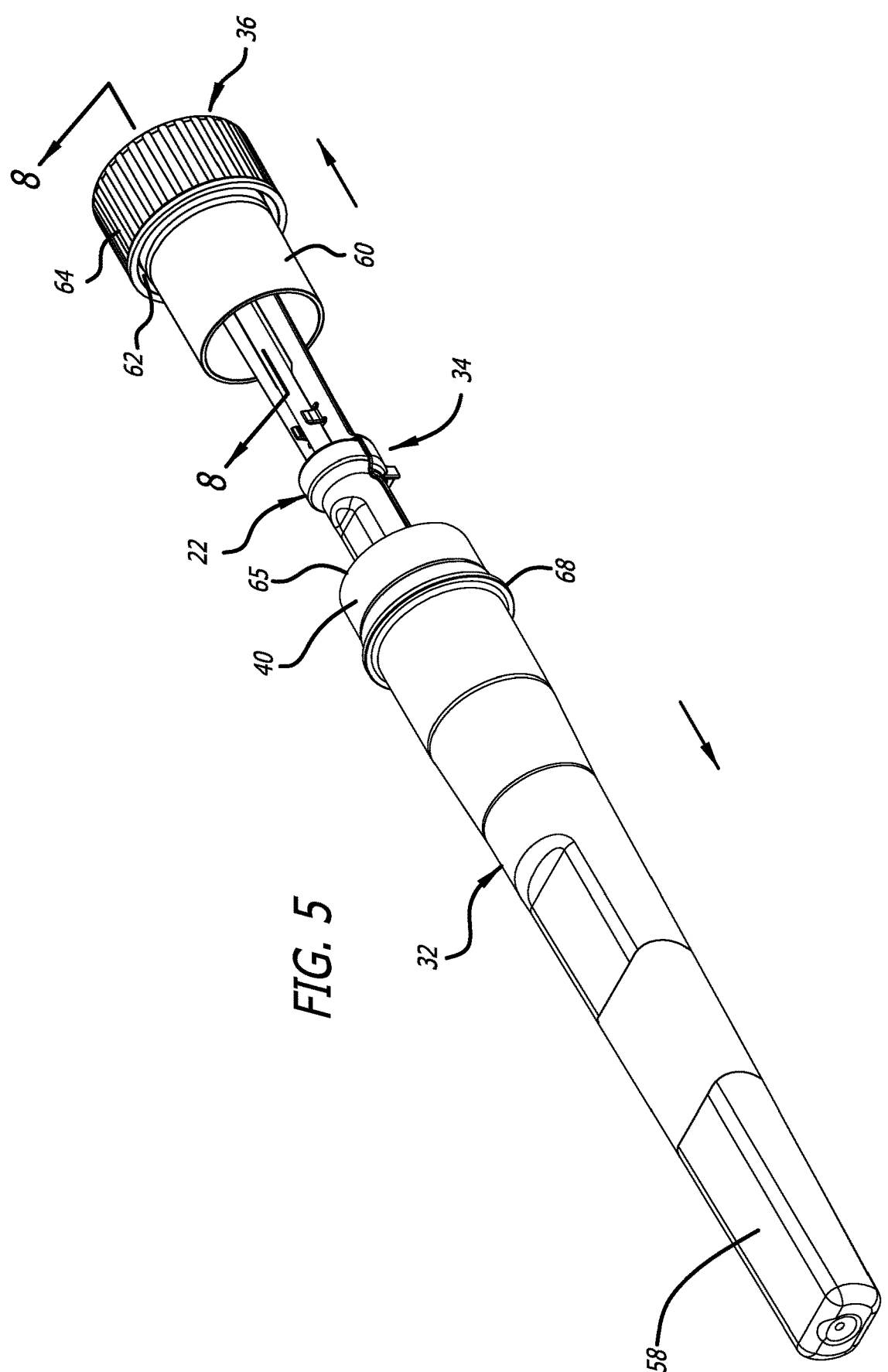
FIG. 5 is a perspective view from a distal end during removal of the compact IOL delivery system from the sterile package.

FIGS. 4 and 5 are perspective views from the proximal and distal ends of the sterile package 20 after a step of breaking the second tamper-evident strip 54 and partial removal of the IOL delivery system 22 from the sterile package. The IOL delivery system 22 is retained in the transfer tray 34 in a manner which keeps the subassembly together until manual separation. To open the sterile package 20, a user rotates the proximal cap 36 either clockwise (CW) or counterclockwise (CCW), as shown. This ruptures the second tamper evident strip 54, leaving a portion on the container 32 and a portion on the cap 36. Although threading may be used, in one aspect of the invention the cap 36 engages the tubular mouth 40 of the container 32 without threading, such that a user can rotate the cap in either direction and simply pull the cap proximally to remove. The cap 36 is thus may be held on by a friction fit. The closure between the cap 36 and the tubular mouth 40 of the container 32 may be designed to confirm package seal integrity by means of a required opening torque, force or otherwise quantifiable measure. As will be explained below, the subassembly of the IOL delivery system 22 and transfer tray 34 is also pulled out of the container 32 when the cap 36 is removed, by virtue of engagement of the subassembly within the cap.

It should be noted that the cap 36 in the embodiment of the invention shown in FIG. 4 can be rotated freely in either direction, as shown, without also rotating the subassembly of the IOL delivery system 22 and transfer tray 34. This allows for the subassembly to have a single position within the container 32. The container 32 has a non-circular distal end—in the illustrated embodiment the end has two opposed flat faces 58 in an otherwise tapered tube. The flat faces 58 enable the container to be placed on a shelf or other support surface in one of two orientations—an upright or an upside down orientation. At the same time, the cap 36 engages the open mouth 40 in a manner which permits free relative rotation therebetween without rotating the subassembly of the delivery system 22 and transfer tray 34 within the container 32. Therefore, the identification label 52 is desirably stored up so that the IOL delivery system 22 remains above and is supported by the transfer tray 34. Rotating the cap 36 breaks the second tamper-evident strip 54 but does not rotate the subassembly.

Figures 7, 8, 8A:
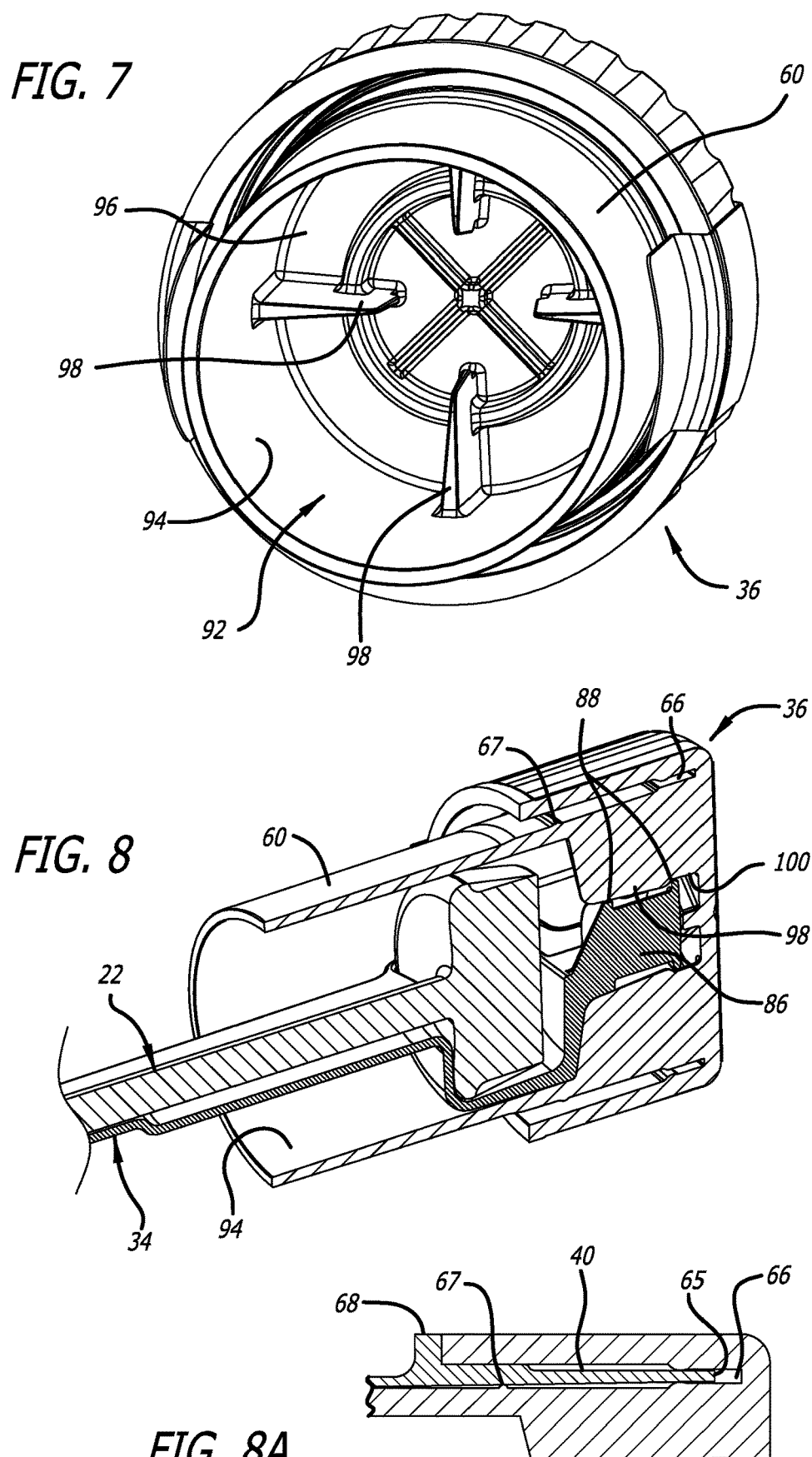
FIG. 7 is a perspective view of an inner cavity of the cap of the compact, sterile package.
FIG. 8 is a longitudinal sectional view through a proximal end of the compact, compact IOL delivery system and transfer tray engaged within the sterile package cap.
FIG. 8A is an enlarged sectional view showing sealing regions between the cap and package container.

An exemplary embodiment of the seal between the container 32 and a proximal cap 36 includes the tubular mouth 40 which is elongated in a first length in a distal direction and has a diameter that closely fits around an elongated tubular skirt 60 of the cap 36. As seen in FIG. 5, the cap 36 defines an annular space 62 between a tubular gripping portion 64 and the skirt 60. The skirt 60 extends within the tubular mouth 40 a sufficient distance for the mouth to extend into the annular space 62. There are two annular regions of interference contact between the cap 36 and tubular mouth 40 for sealing. A first or primary sealing region is from contact between the distal end 65 of the tubular mouth 40 (see FIG. 5) and a narrowed inner end 66 of the annular space 62 of the cap 36, best seen in FIG. 8. FIG. 8 also shows an external rib 67 on the skirt 60 and within the annular space 62 that contacts and seals against an inner lumen of the tubular mouth 40 to provide a secondary sealing region. Both sealing regions are provided by material interference fits, though elastomeric O-rings or the like might be also utilized. Likewise, a permeable (peel away) film could be applied in the mouth of the container to generate the sterile barrier, as an alternative. This provides a redundant sterile seal for the package 20. Finally, a distal end of the tubular gripping portion 64 contacts an external flange 68 on the container 32 to provide a stop when assembling the cap 36 onto the container 32. The tubular mouth 40 thus has a first length in a distal direction from the open distal end thereof to the flange 68. The first length is approximately equal to an axial dimension of the gripping portion 64, such that the open mouth fits entirely within the cap 36.

Figures 9, 10:
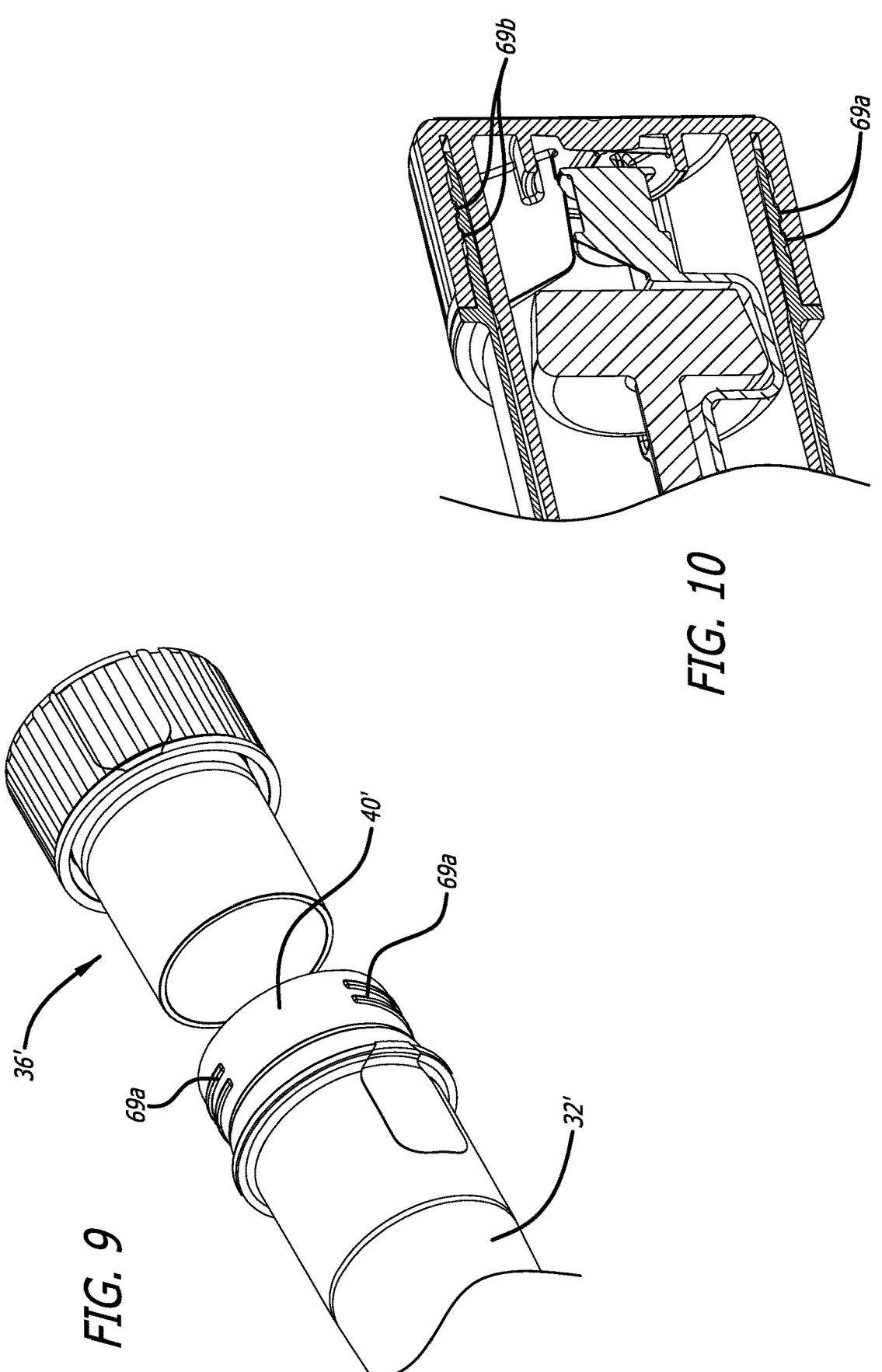
FIG. 9 is a perspective view of an alternative sterile package cap and container coupling solution.
FIG. 10 is a longitudinal sectional view through a proximal end of the IOL delivery system and transfer tray engaged within the cap.

FIG. 9 is a perspective view of an alternative sterile package cap 36' and container 32' coupling solution, and FIG. 10 is a longitudinal sectional view through a proximal end of the IOL delivery system and transfer tray engaged within the alternative cap 36'. In this embodiment, the container mouth 40' has a plurality of external circumferential partial ribs 69a that engage and interfere with similarly sized and shaped internal ribs 69b within the cap 36', as seen in FIG. 10. The external and internal ribs 69a, 69b each extend roughly 90° or slightly less, and are diametrically opposed on each element so that the cap 36' must be rotated 90° to disengage the interfering ribs. Once the cap 36' is rotated 90° it may be directly pulled off of the container mouth 40'. Sealing regions as described above are also provided.

In general, the transfer tray 34 should be configured to retain the delivery system securely. In one aspect, the tray is also configured to retain the plunger rod 28 in a retracted position and prevent significant movement of the plunger into the delivery system 22 during shipping and storage. In another aspect, the transfer tray 34 is configured to retain the delivery system, but the delivery system itself is configured to prevent significant movement of the plunger during shipping and storage.

Figure 11:
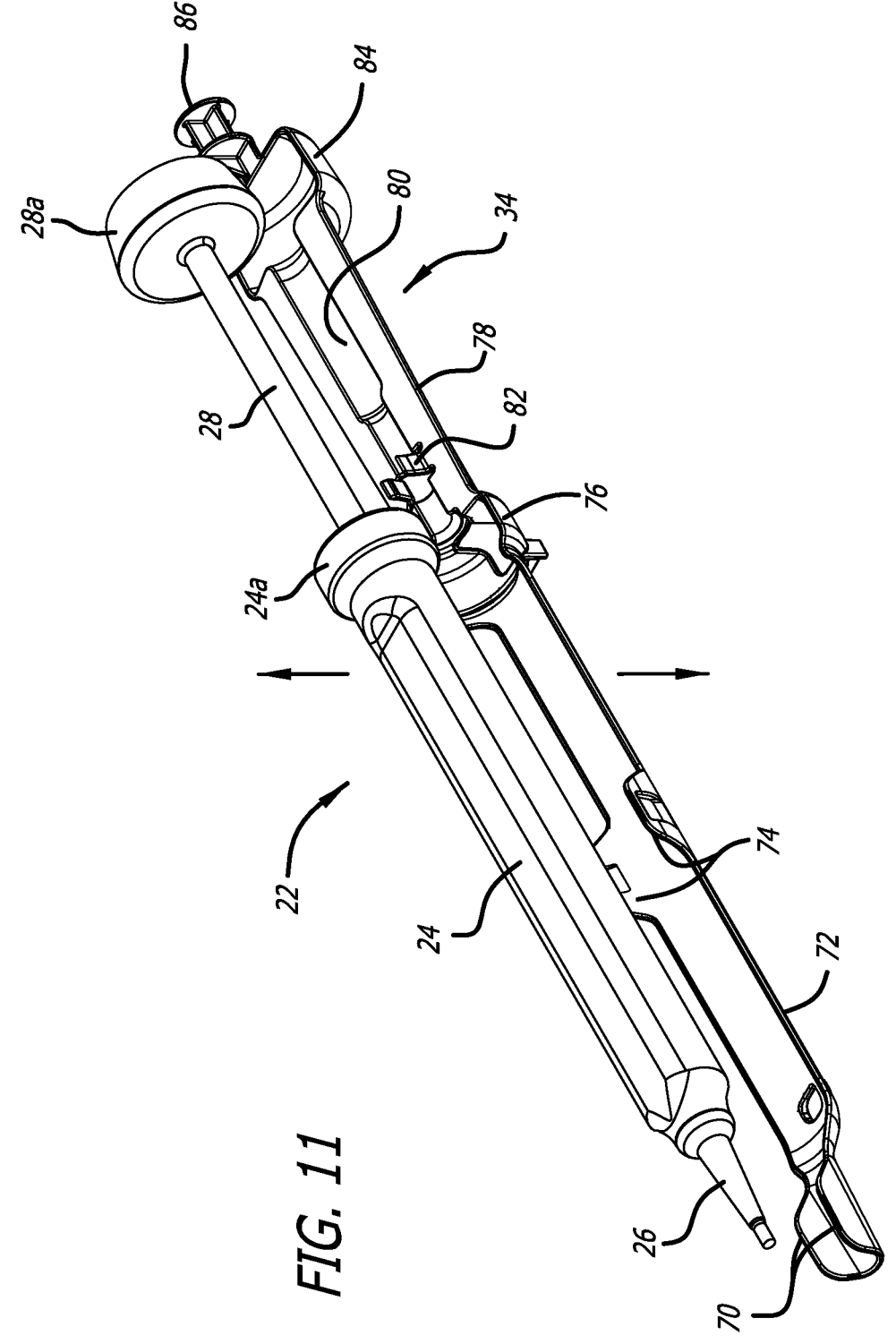
FIG. 11 is a perspective view illustrating a final step of removal of the compact IOL delivery system from the transfer tray prior to use.

With reference back to FIG. 2 and also FIGS. 6 and 11, one embodiment of a transfer tray 34 is shown having specific contours which match the delivery system 22. First of all, the tray 34 is elongated so that it has a longer dimension than the delivery system 22 with the plunger rod 28 retracted as shown. The tray 34 comprises a molded thin plastic sheet on which the delivery system 22 is supported and includes several features for retaining the delivery system. In general, the transfer tray 34 has multiple shaped female recesses which match male shapes on the delivery system, and a retention portion that may be formed by at least one pair of retention wings that resiliently flex and hold the delivery system 22 on the tray. It should be understood that such retention wings may take many forms, and are essentially a resilient portion of the transfer tray which flexes to accept and hold the delivery system. From the distal to the proximal end, the tray 34 has a pair of upstanding walls 70, a concave elongated trough segment 72, a first pair of retention wings 74 in the middle of the trough segment, a first recess 76, an elongated flat portion 78 having a central indent 80, a second pair of retention wings 82, a second recess 84, and a proximal handle 86.

It will be appreciated by one of ordinary skill in the art that the features described herein are not all required elements. By way of example, and not of limitation, the trough segment 72 may be planar, the walls or one or both sets of retention wings may be removed, and/or the elongated flat portion may be configured without a central indent. What is important is that the tray 34 is appropriately configured to securely hold the delivery system 22 during shipping, handling and storage.

The subassembly of the IOL delivery system 22 held within the transfer tray 34 is seen in FIG. 6. The trough segment 72 is concave and shaped to closely receive a syringe body 24, with the first pair of retention wings 74 being cantilevered and positioned to resiliently hold onto the syringe body. In a similar manner, the central indent 80 of the flap portion 78 is concave and shaped to closely receive the push rod 28, with the second pair of retention wings 82 being cantilevered and positioned to resiliently hold onto the push rod. The two pairs of flanking retention wings 74, 82 thus flex apart and hold onto the IOL delivery system 22. The upstanding walls 70 flank or surround and physically protect the tapered distal end 26 of the syringe body 24 from damage. The first recess 76 is sized and shaped to closely receive an outward circular flange 24a on the proximal end of the syringe body 24, while a second recess 84 is sized and shaped to closely receive a thumb rest 28a on the proximal end of the push rod 28.

The particular contours of the illustrated transfer tray 34 are specific to the IOL delivery system 22 shown, and of course may be modified for other IOL delivery systems. For instance, the delivery system 22 has a screw-type of push rod 28 which may be replaced with a push-type of plunger rod. Push-type plunger rods usually have a finger grip at the back end of the syringe barrel, and so a cavity or trough to accommodate such structure would be provided in the transfer tray. Those of skill in the art will recognize numerous such permutations.

As mentioned, the subassembly of the IOL delivery system 22 held within the transfer tray 34 engages the proximal cap 36 so that when the cap is separated from the container 32, subassembly is pulled from within the container. FIGS. 6-9 illustrate one configuration for coupling the subassembly to the cap 36.

The proximal handle 86 of the transfer tray 34 is formed with a pair of radially-oriented circular flanges 88 that are axially spaced apart and connected by a central shaft member 90. The shaft member 90 is actually formed by a pair of axially-extending walls that intersect in a crossed configuration (e.g., at 90°). The circular flanges 88 are sized to engage internal features of the proximal cap 36, as will be shown.

With reference to FIG. 7, an inner cavity 92 of the cap 36 is defined by the lumen 94 of the distal skirt 60 that leads to a proximal wall 96 having a number of circumferentially-spaced radially-oriented ribs 98 projecting axially therefrom. The ribs 98 project inward from the lumen 94 and their inner ends together define a circle of revolution and a channel having a diameter approximately equal to the diameter of the circular flanges 88. The axial dimension of the ribs 98 is slightly greater than the spacing between the flanges 88. Therefore, as seen in FIG. 8, the proximal handle 86 may be inserted within the channel defined by the ribs 98 which hold it in an interference fit; therefore, also retaining a portion of the subassembly of the IOL delivery system 22 and transfer tray 34 within the cavity 92 of the cap 36. A closer examination of the sectional view of FIG. 8 shows that each of the ribs 98 is shaped to facilitate this retention. Each of the ribs 98 has a slightly tapered configuration, becoming radially larger in a proximal direction, until a relief cutout 100 at proximal end. This enables the first circular flange 88 to flex the ribs 98 until it "pops" into the cutout 100, while the second circular flange 88 is in close contact with the ribs. This arrangement provides a nominal holding force while stabilizing the subassembly of the IOL delivery system 22 and transfer tray 34 along a central axis so that it is held securely (i.e., not loosely).

It should be noted that the particular coupling arrangement between the transfer tray 34 and the cap 36 is merely exemplary, and various others are contemplated. Preferably, the transfer tray 34 attaches to the cap 36 via a friction fit, as shown, though one of skill in the art would appreciate that there are other ways to achieve a friction fit between the transfer tray 34 and the cap 36. In one aspect, more positive connections may be used, such as a detent that must be removed or the like. The coupling should be easy to disengage to avoid a struggle at the moment when the subassembly of the IOL delivery system 22 and transfer tray 34 is transferred into the sterile space, but secure enough to avoid the subassembly easily falling out of the cap. In one embodiment, the cap 36 with skirt 60 may be sufficiently long (extend sufficiently into the container 32) so that when the container 32 is removed the cap can support the subassembly. For instance, the skirt 60 may have a length of at least 1.0-4.0 cm. The skirt 60 is meant to protect the IOL delivery system 22 from incidental contact from the transfer operation by the non-sterile side technician offering a sterile device to the sterile side technician.

FIG. 6 shows the subassembly being separated from the proximal cap 36 of the sterile package 20 at the moment of transfer between a non-sterile environment to a sterile environment. The hands of two technicians are shown, with at least the left hand under the subassembly of the IOL delivery system 22 and transfer tray 34 being sterile. The right hand may be of someone who is clean, but not necessarily sterile per surgery conventions, and as such they only touch the cap 36, and preferably just the gripping portion 64 and not the tubular skirt 60. As long as the subassembly does not easily fall out, and the coupling with the cap 36 is relatively easy to disengage, the users have an easy time simply passing off the subassembly into the sterile surgery space.

FIG. 12 is a perspective view of a compact IOL delivery system 120 according to another aspect of the invention, where the compact IOL delivery system 120 is exploded from the sterile package components, including the container 32, the transfer tray 34, and the proximal cap 36. The sterile package accommodates the alternative IOL delivery system 120 in the same manner as described herein; FIG. 12 being included to emphasize that the package may be used with different IOL delivery system configurations.

The first alternative IOL delivery system 120 is ready-to-use, in that one need only open the sterile package and the system 120 is primed to delivery an IOL into an eye in an ophthalmic surgical procedure once the surgeon has complied with any manufacturer instructions, like hydration. In this case, the delivery system 120 is formed of two parts coupled together, rather than the integrated system 22 described above. Namely, the delivery system 120 has a handpiece 122 with plunger rod 124, which is coupled to an IOL cartridge 126 on a distal end. The IOL cartridge 126 contains an IOL therein, and is pre-loaded with the IOL prior to being coupled to the handpiece 122. A number of such coupled systems exist in the field, such as the TECNIS Simplicity® Delivery System available from Johnson & Johnson Surgical Vision, Inc. of Irvine, CA. It should be noted that the transfer tray 34 is shown unmodified from the version described for the first delivery system 20, but is desirably contoured to match the alternative IOL delivery system 120. In this case, the two systems are relatively similar and only slight modifications would be needed. That is, the transfer tray 34 has multiple shaped female recesses which match male shapes on the delivery system 120.

FIG. 13 is a perspective view of a second alternative IOL delivery system 130 exploded from the sterile package components, again including the container 32, the transfer tray 34, and the proximal cap 36. The sterile package accommodates the alternative IOL delivery system 130 in the same manner as described herein; FIG. 13 also being included to emphasize that the package may be used with different IOL delivery system configurations.

The second alternative IOL delivery system 130 is not ready-to-use, in that must couple an IOL delivery cartridge to the system 130 prior to an ophthalmic surgical procedure. The delivery system 130 is formed of a handpiece 132 with plunger rod 134, and is adapted to be coupled to an IOL cartridge on a distal end. For instance, the distal end includes a pair of spaced apart fingers 136 that have slots for receiving and retaining an IOL cartridge (not shown). The cartridge may have an IOL pre-loaded therein, or a second step of inserting an IOL into the cartridge may be needed. Once the IOL cartridge is coupled to the handpiece 132, the system 130 is ready to use. A number of such systems exist in the field, such as the Unfolder® or Unfolder Vitan™, both available from Johnson & Johnson Surgical Vision, Inc. of Irvine, CA. It should again be noted that the transfer tray 34 is shown unmodified from the version described for the first delivery system 20, but is desirably contoured to match the alternative IOL delivery system 130. That is, the transfer tray 34 has multiple shaped female recesses which match male shapes on the delivery system 130.

Figure 14:
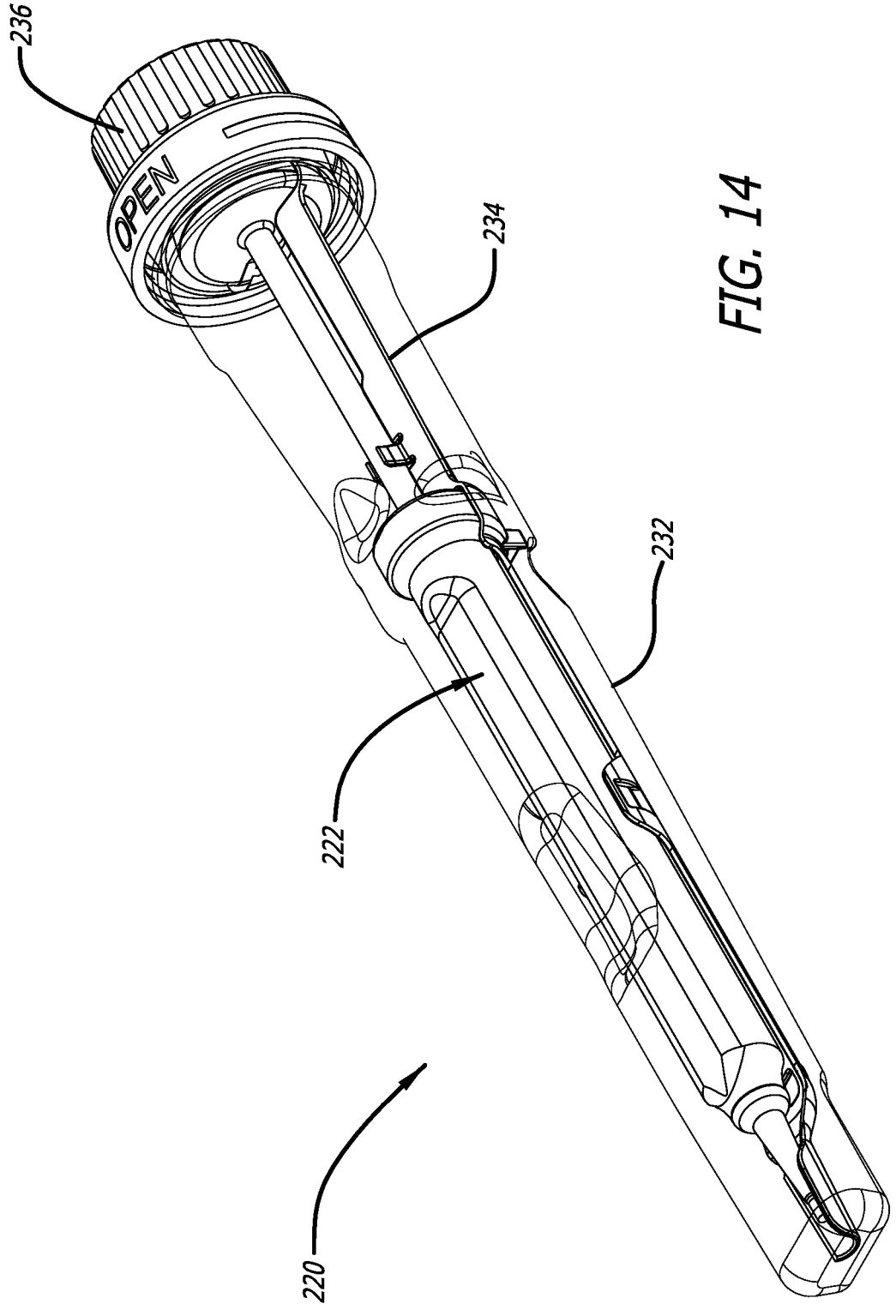
FIG. 14 is a perspective view from a distal end of an alternative compact intraocular lens (IOL) delivery system sterile package in a closed configuration.
Figure 15:
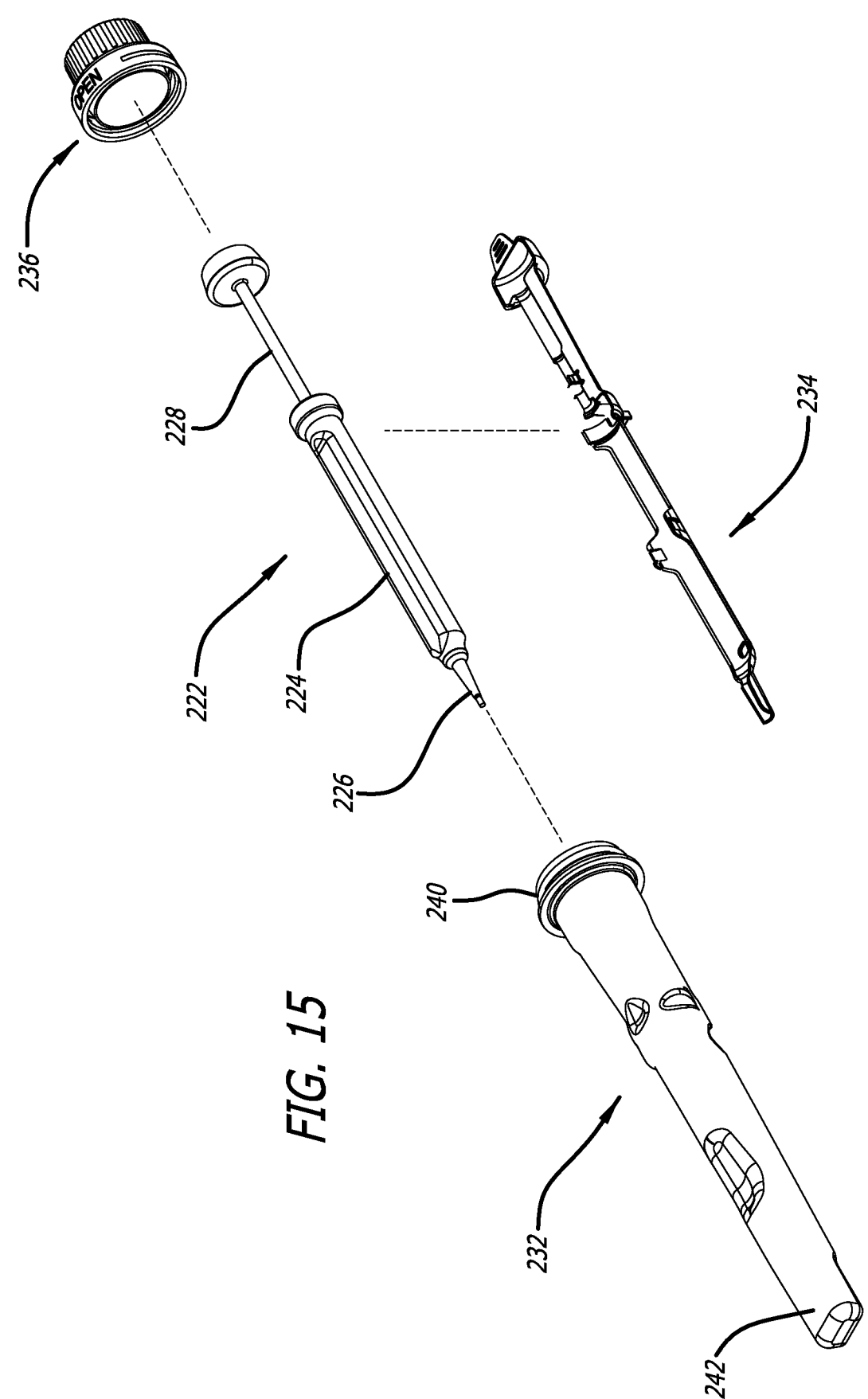
FIG. 15 is a perspective view of a compact IOL delivery system exploded from the components of the sterile package of FIG. 14.

FIG. 14 is a perspective view from a distal end of an alternative compact intraocular lens (IOL) delivery system sterile package 220 in a closed configuration, while FIG. 15 shows the IOL delivery system 222 exploded from the components of the sterile package. As described above, the IOL delivery system 222 comprises a syringe-like integrated assembly of an injector and an IOL (not shown). More particularly, the delivery system 222 includes a syringe body 224 having a tapered distal tip 226. An IOL may be placed within the syringe body 224 at the time of surgery, or may be pre-assembled therein. A plunger rod 228 is then used to urge the IOL from within the syringe body 224 through the distal tip 226 into the patient's eye.

Figure 18:
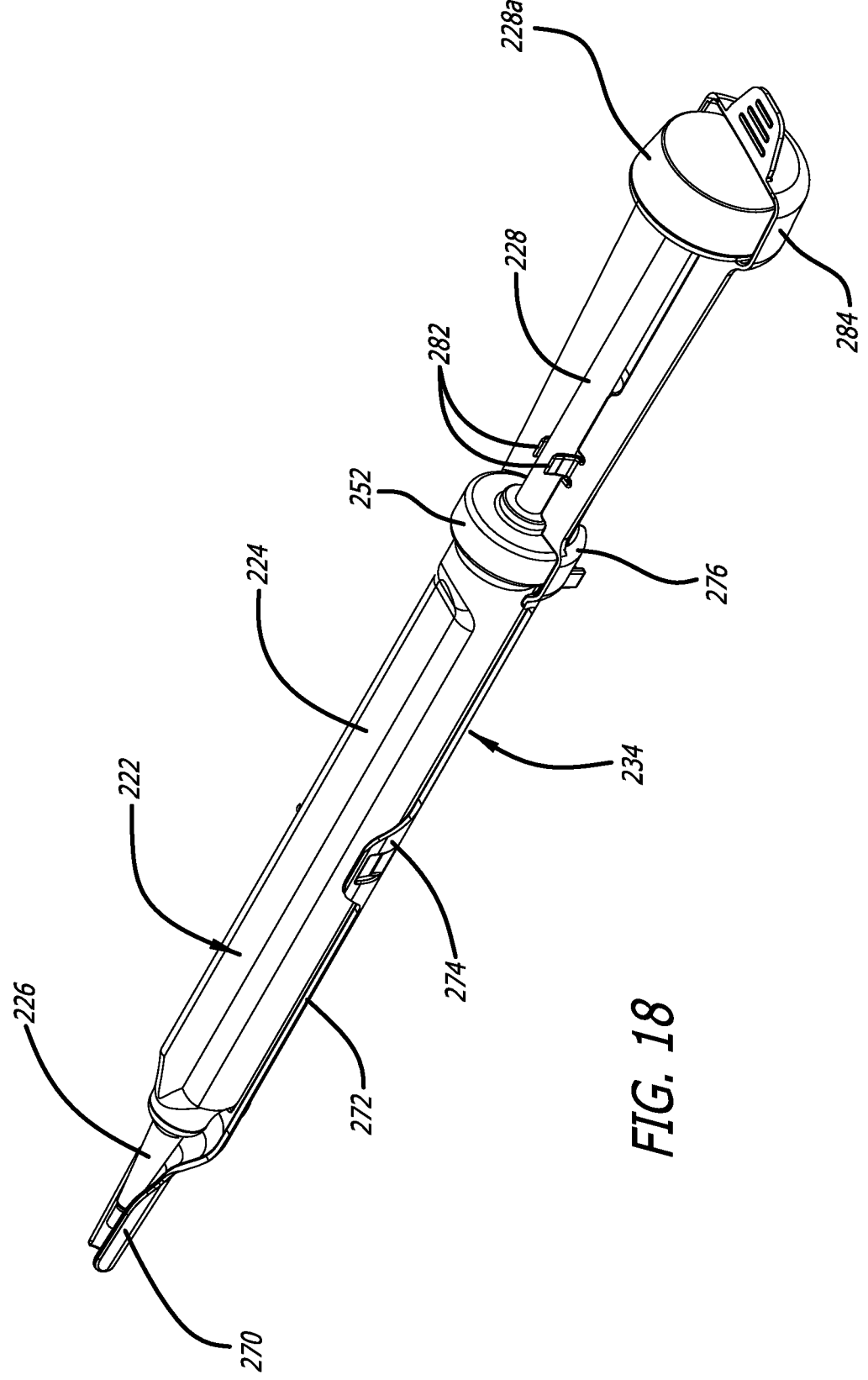
FIG. 18 is a perspective view of the alternative compact IOL delivery system and transfer tray of FIG. 14 after removal from the sterile package.

The sterile package 220 shown in FIG. 15 primarily comprises an elongated, generally tubular container 232, a transfer tray 234, and a proximal end cap 236. The transfer tray 234 is shaped to receive and retain the IOL delivery system 222 in a subassembly, as seen in FIG. 18, and the generally tubular container 232 has an inner cavity with the diameter and length sufficient to receive the subassembly. The generally tubular container 232 is gradually tapered from a wide, circular open mouth 240 at a proximal end to a narrow, closed distal end 242. Though a tapered profile for the container 232 serves to constrain the subassembly from movement, other solutions such as inner bulkheads or the like may be used with a cylindrical or otherwise non-tapered profile. The inner cavity of the container 232 may be shaped to closely receive the subassembly of the IOL delivery system 222 and transfer tray 234 such that little or no relative movement is permitted when the subassembly is received in the container.

One of ordinary skill in the art will appreciate that the in an alternate embodiment of the invention, the use of the tray 234 may be optional. In such an embodiment, a protective feature or cap would be included to protect distal tip 226 from damage caused by abutting against tubular container 232. Protective features may also be included to ensure that the proximal end of the plunger rod is not inadvertently advanced. In one aspect of the invention (not shown), protrusions on the tubular container may align with indentations on the IOL delivery system. The IOL delivery system may be released from the tubular container by gentle pressure, or squeezing, thus flexing the tubular container.

In the previous embodiments, retraction of the cap from the sterile package container also served to pull the subassembly of the IOL delivery system and transfer tray from within the container, in a single action. The alternative sterile package 220 shown in FIG. 14 requires two steps to remove the subassembly of the IOL delivery system 222 and transfer tray 234 from the container 232.

Figures 16, 17:
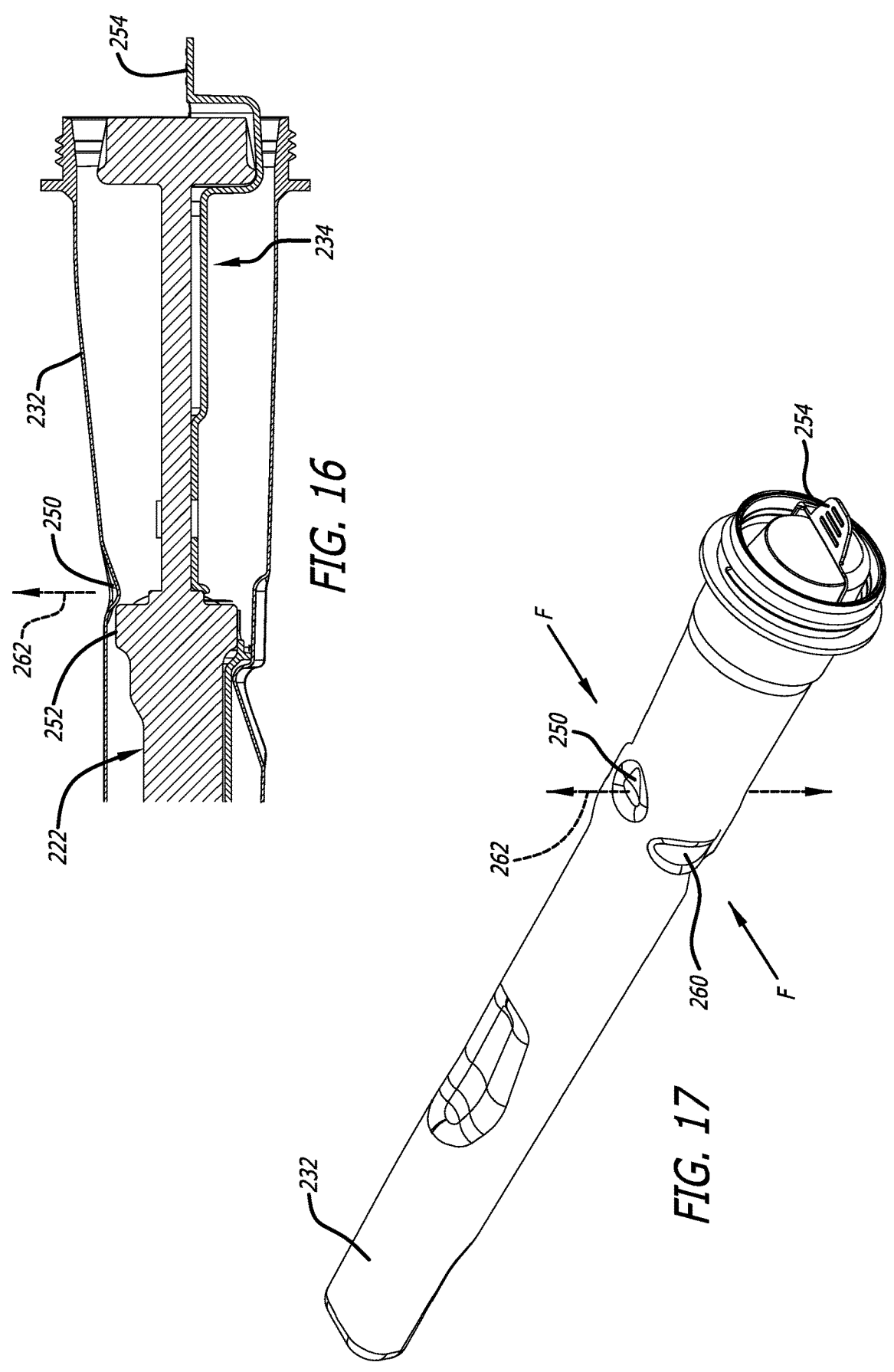
FIG. 16 is a longitudinal sectional view through a proximal end of the alternative compact IOL delivery system and transfer tray of FIG. 14 engaged within a sterile package cap'
FIG. 17 is a perspective view from a proximal end of the alternative compact IOL delivery system of FIG. 14 prior to removal of the delivery system and transfer tray from the sterile package.

FIG. 16 is a longitudinal sectional view through a proximal end of the alternative IOL delivery system 222 and transfer tray 234 of FIG. 14 within the container 232. The cap 236 has been removed, such as by unscrewing mating threads, rotating and pulling the cap off, or simply pulling the cap off—all versions being conceivable. The subassembly of the IOL delivery system 222 and transfer tray 234 fits closely within the container 232 and a small indent 250 formed in one wall of the container 232 retains the subassembly in place when the cap 236 is removed. In the embodiment of the invention shown, the indent 250 is located just proximally to an enlarged circular flange 252 on the proximal end of the syringe body 224, and extends radially inward far enough to prevent the syringe body 224, and thus the subassembly, from falling out of the container 232. It will be appreciated that the location of indent 250 will be based on the design of the container and the IOL delivery system, so that the indent is appropriately placed to secure the IOL delivery system in the container.

The material and wall thickness of the container 232 allow a technician to simply pull the subassembly of the IOL delivery system 222 and transfer tray 234 out of the container, causing the circular flange 252 to push or cam the indent 250 outward as it passes. A proximal tab 254 on the proximal end of the tray 234 is helpful in this regard. Alternatively, the container 232 maybe manipulated to permit the subassembly to slide out by gravity, without requiring any force and without touching the subassembly. FIG. 17 is a perspective view from a proximal end of the alternative package showing inward force arrows F applied by squeezing on two lateral sides of the container 232, such as at opposed finger indents 260. Squeezing the container 232 in this fashion causes outward bowing or flexing of the container 232 at the upper indent 250, as indicated by the dashed upward arrow 262. This releases the subassembly of the IOL delivery system 222 and transfer tray 234 to be simply slid out of the container 232 without touching the subassembly. This option for removal of the subassembly protects the IOL delivery system 222 from incidental contact during the transfer operation by the non-sterile side technician offering a sterile device to the sterile side technician.

After removal from the sterile package, the subassembly of the IOL delivery system 222 held within the transfer tray 234 is seen in FIG. 18. A trough segment 272 is concave and shaped to closely receive the syringe body 224, with a first pair of retention wings 274 being cantilevered and positioned to resiliently hold onto the syringe body. In a similar manner, a second pair of retention wings 282 is cantilevered and positioned to resiliently hold onto the push rod 228. The two pairs of flanking retention wings 274, 282 thus flex apart and hold onto the IOL delivery system 222. Upstanding walls 270 flank or surround and physically protect the tapered distal end 226 of the syringe body 224 from damage. A first recess 276 is sized and shaped to closely receive the outward circular flange 252 on the proximal end of the syringe body 224, while a second recess 284 is sized and shaped to closely receive a thumb rest 228a on the proximal end of the push rod 228.

While the invention has been described in its preferred embodiments, it is to be understood that the words which have been used are words of description and not of limitation. Therefore, changes may be made within the appended claims without departing from the true scope of the invention.

What is claimed is:

1. A sterile package for an intraocular lens delivery system, comprising:
  an intraocular lens delivery system;
  a generally tubular container elongated along a central axis and having a closed distal end and a tubular open mouth at a proximal end, the open mouth being one end of a lumen defined by a wall of the tubular container that extends a first length in a distal direction;
  a proximal cap adapted to engage and seal the open mouth of the container, the cap having a gripping portion on a closed proximal end surrounding and spaced outwardly from a tubular skirt that projects in a distal direction, the tubular skirt having an inner cavity and an outer diameter which fits closely within the lumen of the container, the wall of the tubular container being dimensioned to contact and form a first seal with the cap; and
  a transfer tray configured to receive and retain the delivery system and form a subassembly therewith sized to fit within an inner cavity of the container, the transfer tray comprising a proximal handle sized to fit within the inner cavity of the tubular skirt of the cap and extend to the proximal end thereof, wherein the delivery system is sized to fit within an inner cavity of the container and a sterile condition is maintained by engaging the cap to the open mouth, and wherein a user may open the cap and deliver the delivery system to a sterile environment without touching the delivery system, and wherein the inner cavity of the cap comprises one or more radially-directed ribs on an inner surface configured to define a channel that receives and retains in an interference fit the proximal handle of the transfer tray.

2. The sterile package of claim 1, wherein the first seal is formed by contact between an exterior rib portion on the tubular skirt and the wall of the tubular container.

3. The sterile package of claim 1, wherein the first seal is formed by contact between the open mouth and an inner surface within the gripping portion of the cap.

4. The sterile package of claim 3, wherein a second seal is formed by contact between an exterior rib portion on the tubular skirt and the wall of the tubular container.

5. The sterile package of claim 1, wherein the transfer tray comprises multiple shaped female recesses which match male shapes on the delivery system and at least one retention portion which resiliently flexes around and holds the delivery system in place on the transfer tray.

6. The sterile package of claim 5, wherein the delivery system has a syringe body and a plunger rod, and the at least one retention portion includes at least one pair of retention wings that hold one part of the delivery system selected from the group consisting of the syringe body and the plunger rod.

7. The sterile package of claim 6, wherein the delivery system has a distal tapered tip configured to be inserted into the patient's eye, and wherein the transfer tray includes a spaced apart pair of upstanding walls that flank and physically protect the tapered tip.

8. The sterile package of claim 5, wherein the transfer tray has a length greater than an axial length of the delivery system.

9. The sterile package of claim 1, wherein the sterile package further includes a tamper-evident strip adhered to both the gripping portion of the cap and the container which must be broken or severed before the cap can be removed from the container.

10. The sterile package of claim 1, wherein the sterile package further includes a tamper-evident strip extending longitudinally over an entire length of the container and wrapping around the proximal end of the cap.

11. The sterile package of claim 10, further comprising a second tamper-evident strip, wherein the sterile package further has a folded identification label secured to an exterior of the container and adapted to be pulled away from the container to view the identification thereon, wherein the second tamper-evident strip extends over the identification label and the second tamper-evident strip must be removed or torn prior to viewing the identification on the identification label.

12. The sterile package of claim 1, wherein the container has a non-circular distal portion such that an assembled sterile package is configured to rest on a support surface in one of two orientations—an upright or an upside down orientation—and the cap engages the open mouth in a manner which permits free relative rotation therebetween without rotating the delivery system within the container.

13. The sterile package of claim 1, wherein the inner cavity of the container has an inwardly-directed portion that interferes with and prevents the delivery system from sliding out of the inner cavity when the cap is removed.

14. The sterile package of claim 13, wherein the container walls are flexible such that squeezing the container adjacent to the inwardly-directed portion causes the inwardly-directed portion to flex outward and release the delivery system to enable sliding out of the inner cavity without force.

15. A sterile package for an intraocular lens delivery system, comprising:

an intraocular lens delivery system;

a generally tubular container elongated along a central axis and having a closed distal end and a tubular open mouth at a proximal end, the open mouth extending a first length in a distal direction;

a proximal cap adapted to engage and seal the open mouth of the container, the cap having a tubular gripping portion on a closed proximal end and a tubular skirt that projects therefrom in a distal direction, the tubular skirt having an outer diameter which fits closely within the open mouth of the container, and the cap having an inner cavity with a plurality of radially-directed ribs on an inner surface configured to define a channel; and a transfer tray configured to receive and retain an intraocular lens delivery system, the transfer tray having multiple shaped female recesses which match male shapes on the delivery system and at least one pair of retention wings which resiliently flex around and hold the delivery system in place on the transfer tray, the transfer tray further including a proximal handle which fits within a lumen of the tubular skirt of the cap and extends towards the proximal end thereof, the proximal handle being sized to be retained in an interference fit by the channel defined by the ribs within the cap, wherein a subassembly of the delivery system and transfer tray is sized to fit within an inner cavity of the container and maintain a sterile condition by engaging the cap to the open mouth, and wherein a user may open the cap and pull the subassembly from within the container and deliver the subassembly to a sterile environment without touching the subassembly.

16. The sterile package of claim 15, wherein the transfer tray is a molded plastic element, and the proximal handle includes a pair of axially spaced apart circular flanges connected by a longitudinal shaft.

17. The sterile package of claim 16, wherein the radially-directed ribs are tapered so as to be radially larger at a proximal end than at a distal end, such that the channel defined thereby gradually narrows and a relief cutout for each rib is provided at the proximal end thereof, and wherein the proximal handle is configured such that a proximal one of the circular flanges extends past the ribs and into the relief cutout when the transfer tray is pushed into the inner cavity of the cap.

18. The sterile package of claim 15, wherein the delivery system has a syringe body and a plunger rod, and the at least one pair of retention wings holds one part of the delivery system selected from the group consisting of the syringe body and the plunger rod.

19. The sterile package of claim 15, wherein the delivery system has a distal tapered tip configured to be inserted into the patient's eye, and wherein the transfer tray includes a spaced apart pair of upstanding walls that flank and physically protect the tapered tip.

20. The sterile package of claim 15, wherein the sterile package further includes a tamper-evident strip adhered to both the gripping portion of the cap and the container which must be broken or severed before the cap can be removed from the container.

21. The sterile package of claim 15, wherein the sterile package further includes a tamper-evident strip extending longitudinally over an entire length of the container and wrapping around the proximal end of the cap.

22. The sterile package of claim 15, wherein the container has a non-circular distal portion such that an assembled sterile package is configured to rest on a support surface in one of two orientations—an upright or an upside down orientation—and the cap engages the open mouth in a manner which permits free relative rotation therebetween without rotating the subassembly of the delivery system and transfer tray within the container.

23. A method of storing in a sterile condition and delivering to a sterile environment an intraocular lens delivery system, comprising:

providing a sterile package enclosing an intraocular lens delivery system, sterile package including:

a generally tubular container elongated along a central axis and having a closed distal end and a tubular open mouth at a proximal end, the open mouth extending a first length in a distal direction;

a proximal cap adapted to engage and seal over the open mouth of the container, the cap defining an inner cavity;

a transfer tray configured to receive and retain the delivery system, the transfer tray having multiple shaped female recesses which match male shapes on the delivery system and at least one pair of retention wings which resiliently flex around and hold the delivery system in place on the transfer tray, the transfer tray further including a proximal handle which fits within the inner cavity of the cap and extends towards the proximal end thereof; and at least one tamper-evident strip extending across a dividing line between the container and cap which must be broken to disengage the cap from the container, breaking the tamper-evident strip by rotating the cap;

pulling a subassembly of the delivery system and transfer tray out of the container while only touching the cap;

presenting the subassembly to personnel within a sterile environment;

extracting the subassembly from the cap within the sterile environment; and separating the delivery system from the transfer tray prior to performing an ophthalmic surgical procedure.

24. A sterile package for an intraocular lens delivery system, comprising:

an intraocular lens delivery system;

a generally tubular container elongated along a central axis and having a closed distal end and a tubular open mouth at a proximal end, the open mouth being one end of a lumen defined by a wall of the tubular container that extends a first length in a distal direction;

a proximal cap adapted to engage and seal the open mouth of the container, the cap having a gripping portion on a closed proximal end surrounding and spaced outwardly from a tubular skirt that projects in a distal direction, the tubular skirt having an inner cavity and an outer diameter which fits closely within the lumen of the container, the wall of the tubular container being dimensioned to contact and form a first seal with the cap;

a first tamper-evident strip extending longitudinally over an entire length of the container and wrapping around the proximal end of the cap;

a second tamper-evident strip; and a folded identification label secured to an exterior of the container and adapted to be pulled away from the container to view the identification thereon, wherein the second tamper-evident strip extends over the identification label, and the second tamper-evident strip must be removed or torn prior to viewing the identification on the identification label, and wherein the delivery system is sized to fit within an inner cavity of the container and a sterile condition is maintained by engaging the cap to the open mouth, and wherein a user may open the cap and deliver the delivery system to a sterile environment without touching the delivery system.

* * * * *